US005811247A

United States Patent [19]
Aris et al.

[11] Patent Number: 5,811,247
[45] Date of Patent: Sep. 22, 1998

[54] MONOCLONAL ANTIBODIES TO NUCLEOLAR PROTEIN

[75] Inventors: John Aris; Gunter Blobel, both of New York, N.Y.

[73] Assignee: The Rockefeller University, New York, N.Y.

[21] Appl. No.: 203,717

[22] Filed: Feb. 28, 1994

Related U.S. Application Data

[63] Continuation of Ser. No. 995,340, Dec. 22, 1992, abandoned, which is a continuation of Ser. No. 376,435, Jul. 7, 1989, abandoned.

[51] Int. Cl.[6] .................................................. G01N 33/53
[52] U.S. Cl. .................. 435/7.9; 435/7.21; 435/7.31; 435/942; 435/975; 436/548; 436/518; 436/808; 436/811; 530/388.1; 530/388.21; 530/388.5
[58] Field of Search ................................ 435/7.21, 7.23, 435/7.31, 240.21, 172.2, 975, 7.9, 942; 436/548, 518, 808, 811; 530/387.1, 388.1, 388.21, 388.5

[56] References Cited

U.S. PATENT DOCUMENTS 5,310,892  5/1994  Aris et al. ............................... 536/23.5

OTHER PUBLICATIONS

Aris et al. *J. Cell. Biol.* 107: 17–31, 1988.

Lischwe et al. *J. Biol. Chem.* 260(26):14304–14310, 1985.

Ochs et al. *Biol. Cell.* 54(2):123–33, 1985.

Christensen et al. *Exp. Cell Res.* 166: 77–93, 1986.

Schimmang et al, "A yeast nucleolar protein related to mammalian fibrillarin is associated with small nucleolar RNA and is essential for viability", *The EMBO Journal*, vol. 8, No. 13, pp. 4015–4024, 1989.

R. Henríquez et al, The Journal of Biological Chemistry, vol. 265, No. 4, Feb. 5, 1990, pp. 2209–2215.

*Primary Examiner*—Carol A. Spiegel
*Attorney, Agent, or Firm*—Felfe & Lynch

[57] ABSTRACT

The invention relates to a hybridoma cell line which produces a monoclonal antibody which cross reacts with both yeast and human fibrillarin. Diagnostic kits are also described. These are useful in diagnosing diseases such as scleroderma.

8 Claims, 14 Drawing Sheets

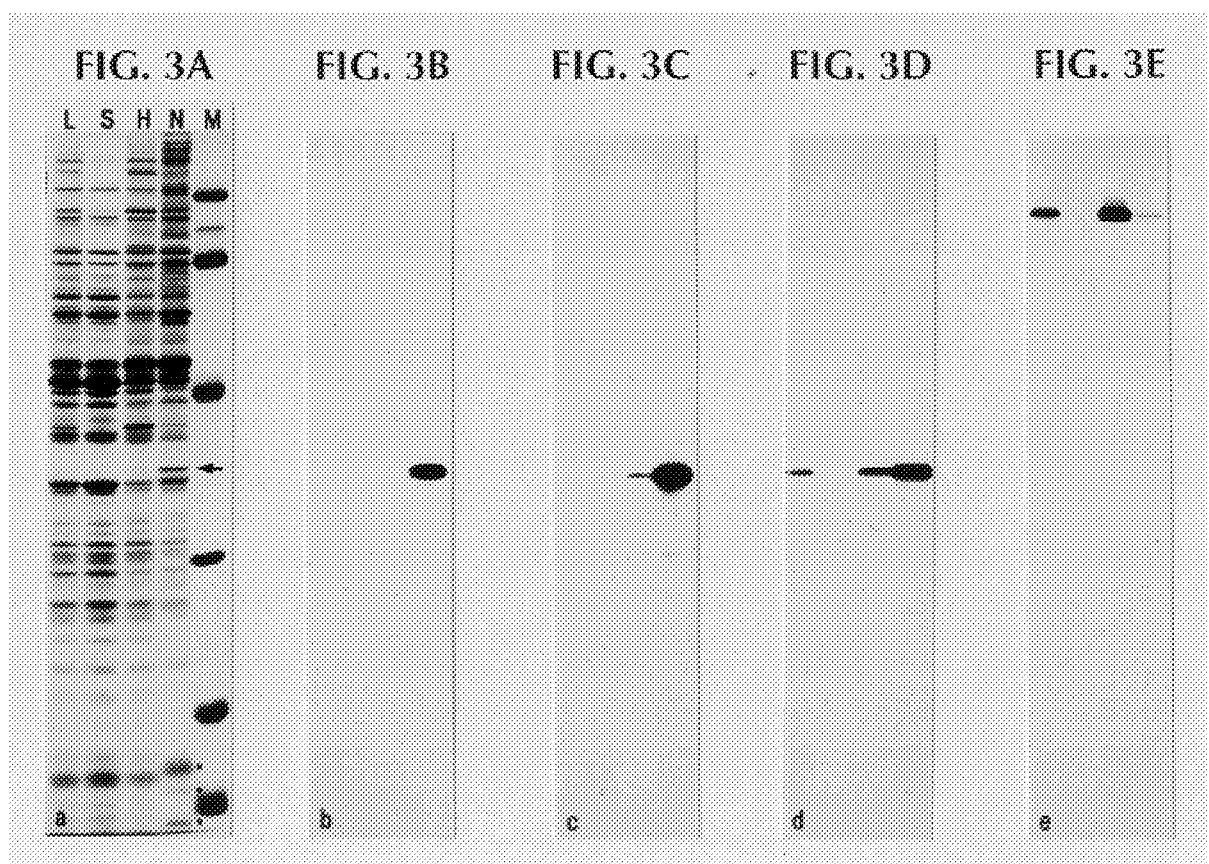

8.0 7.7 7.4 7.1 6.8 6.4 6.1 5.7 5.4

7.9 7.5 7.2 6.9 6.6 6.2 5.8 5.4 5.2

8.0 7.7 7.4 7.1 6.8 6.4 6.1 5.7 5.4

7.9 7.5 7.2 6.9 6.6 6.2 5.8 5.4 5.2

MONOCLONAL ANTIBODIES TO NUCLEOLAR PROTEIN

This application is a continuation of application Ser. No. 07/995,340, filed Dec. 22, 1992, now abandoned, which is a continuation of application Ser. No. 07/376,435, filed Jul. 7, 1989, now abandoned.

This invention was partially made with funds from National Institutes of Health, Public Health Services, Grant GM 10506. Therefore, the U.S. government has certain rights in this invention.

This application concerns anti-nucleolar monoclonal antibodies for use in diagnosis of autoimmune disease.

SUMMARY

We have produced monoclonal antibodies against purified nuclei from the yeast Saccharomyces cerevisiae and have characterized three different antibodies that recognize a protein with an apparent molecular weight of 38,000 termed p38. See in this regard, J. Cell. Biol. 107:17–31 (1988) which is hereby incorporated by reference. Subcellular fractionation shows that virtually all of p38 occurs in the nuclear fraction. High concentrations of salt (1M) or urea (6M) effectively solubilized p38 from a nuclear envelope fraction prepared by digestion of nuclei with DNase. Indirect immunofluorescence demonstrates a crescent shaped distribution of p38 at the inner periphery of the nucleus, with p38 extending between dividing pairs of cells during mitosis. Postembedding immunogold electron microscopy shows decoration of the densely stained "crescent" region of the yeast nucleus, confirming the localization of p38 to the nucleolus. One of the monoclonals, D77, cross reacts on immunoblots with a single protein of molecular weight 37,000 from purified rat liver nuclei. Indirect immunofluorescence localizes this protein to the nucleolus, and shows that it is dispersed throughout the cell during mitosis. The yeast and rat liver nucleolar proteins behave similarly when electrophoresed in two dimensions, and appear to have basic pI (i.e., isoelectric point) values. Analysis of immunological cross-reactivity using D77, and antibodies specific for nucleolar proteins from other sources, suggests that the rat liver protein is fibrillarin, and demonstrates that p38 shares epitopes with fibrillarin, as well as with other vertebrate nucleolar proteins.

DESCRIPTION OF THE DRAWINGS

FIGS. 3(a) through 3(e) show the distribution of p38 in subcellular fractions of yeast. Fractions (50 µg protein each) enriched in low density membranes (L), soluble proteins (S), high density membranes (H), and nuclei (N) were subjected to 10.5% SDS-PAGE, and either stained with Coomassie Blue (a), or analyzed by immunoblotting (b-e). The fractions were collected from a Ficoll 400-step gradient used in preparation of nuclei. The majority of protein p38 occurs in the nuclear fraction (arrow). Immunoblots were probed with monoclonals D77, B15, and A66, and subjected to autoradiography. The monoclonal C56, which reacts with a 98,000-mol-wt protein not found in the nucleus, is presented as a control. Protein molecular weight standards identical to those in FIG. 2 are shown (M). Histones are prominent in the nuclear fraction (solid circles).

DESCRIPTION

Figure 1A:
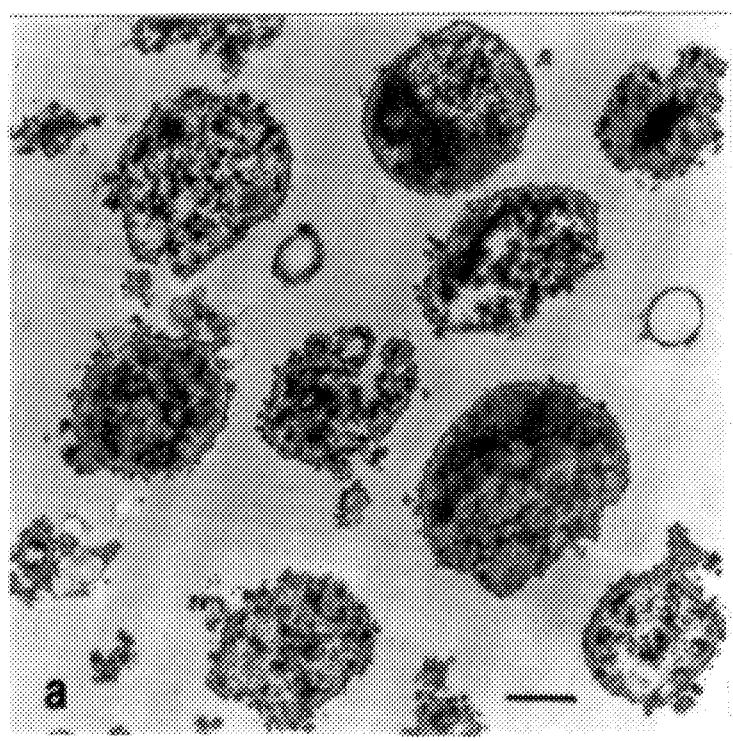
FIGS. 1a and 1b depict electron microscopy of purified nuclei. Nuclei were fixed, embedded, and stained using conventional methods. A typical field of purified nuclei is shown at low magnification in FIG. 1(a). High magnification is present in FIG. 1(b), and the magnification resolves pores (p) in the nuclear envelope and the crescent shaped nucleolus (No.) Bars, 0.5 µm.

The nucleolus of *Saccharomyces cerevisiae* differs from the more familiar vertebrate cell nucleolus in several aspects of its morphology and functional organization. The yeast nucleolus typically has the appearance of a single crescent-shaped region, when viewed by phase contrast (Gordon, C. N., (1977) J. Cell Sci. 24:81–93; Molenaar, I., et al. (1970) Exp. Cell Res. 60:148–156; and Sillevis Smitt, W. W., et al. (1973) Exp. Cell Res. 80:313–321). The crescent-shaped region may occupy a significant portion of the nucleus, and its location is not central but rather juxtaposed to the inner membrane of the nuclear envelope. Electron microscopy reveals a crescent-shaped region that is more densely stained than the area occupied by chromatin, which has a uniform appearance and does not appear to be separated into euchromatic and heterochromatic domains (Gordon, C. N., (1977) Supra; Molenaar, I., et al. (1970) Supra; and Sillevis Smitt, W. W., et al. (1973) Supra). Thus, the region has been commonly termed the "dense crescent" (Carter, B. L. A., (1978) Adv. Microb. Physiol. 17:243–302; Gordon, C. N., (1977) Supra; and Sillevis Smitt, W. W., et al. (1973) Supra). The dense staining of the yeast nucleolus is uniform and does not show the heterogeneous staining that characterizes the subdivisions of the vertebrate nucleolus, which are known as the granular, fibrillar, and fibrillar center components (Fakan, S., et al. (1986) Biol. Cell. 56:189–206; Goessens, G., (1984) Int. Rev. Cytol. 87:107–158; and Hadjiolov, A. A. (1985) Cell Biol. Monogr. 12:1–268). The yeast nucleolus has a simple functional organization. The tandemly repeated ribosomal RNA genes are clustered at the terminus of a single chromosome, number XII, instead of distributed onto multiple chromosomes (Bollon, A. P. (1982) in The Cell Nucleus. rDNA. Part A. Vol. 10. H. Busch and L. Rothblun eds. Academic Press, New York 67–125 and Kuroiwa, T., et al. (1986) Exp. Cell Res. 165:199–206). The organization of the approximately 120 copies (per haploid) of tandemly repeating units of rDNA into the nucleolus organizer region (NOR) is unlike that in higher cells because of the failure of a synaptonemal complex to form in the yeast NOR during meiosis (Moens, P. B., et al. (1985) Chromosoma (Berl.) 91:113–120).

On the other hand, the yeast nucleolus resembles the nucleolus of higher eucaryotes in terms of one of its main functions, the synthesis of rRNA molecules and the assembly of preribosomal particles (Carter, B. L. A. (1978) Supra; and Warner, J. R. (1982), in The Molecular Biology of the Yeast Saccharomyces, Metabolism and Gene Expression, J. N. Strathern, E. W. Jones and J. R. Broach, Cold Spring Harbor Laboratory, Cold Spring Harbor, N.Y. 529–560). Both 37S and 28S ribosomal precursor RNAs are highly enriched in the dense crescent (Sillevis Smitt, W. W., et al. (1973) Supra). Pulse labeling with uracil and high-resolution autoradiography show that label is predominantly incorporated into 37S RNA, and results in a majority of grains over the dense crescent. In terms of structure, the yeast nucleolus contains a fibrillar meshwork similar to that in higher cell nucleoli but embedded in an electron-dense background (Molenaar, I., et al. (1970) Exp. Cell Res. 60:148–156).

Studies of the nucleolus from many species of vertebrates provide more detailed information about the role of this organelle in the synthesis and maturation of rRNA molecules and preribosomal particle assembly (Hadjiolov, A. A. (1985) Supra and Warner, J. R. (1982) Supra). Knowledge of these processes has been obtained from studies of the rRNA intermediates and products involved, and detailed information exists on the organization of the repeated rRNA genes (Hadjiolov, A. A. (1985) Supra). Electron microscopic examination of the vertebrate nucleolus reveals three morphologically distinct regions: the granular and fibrillar components, and the fibrillar centers (Goessens, G. (1984) Int. Rev. Cytol. 87:107–158 and Hadjiolov, A. A. (1985) Cell Biol. Monogr. 12:1–268). Preribosomal particles in different stages of assembly are located within the granular component (Goessens, G. (1984) Supra; and Hadjiolov, A. A. (1985) Supra and Hügle, B., et al. (1985) J. Cell Biol. 100:873–886). The fibrillar component is thought to be the site of pre-rRNA processing (Goessens, G. (1984) Supra and Hadjiolov, A. A. (1985) Supra). The fibrillar centers are the locations at which RNA polymerase I is present in interphase cells, and are considered the sites of nascent rRNA transcription (Scheer, U., et al. (1984) Proc. Natl. Acad. Sci. USA 81:1431–1435). Ribosomal DNA occurs in the fibrillar centers, indicating that they are the interphase equivalent to the mitotic NOR (Hadjiolov, A. A. (1985) Supra).

Some of the proteins in each of these regions have been identified, as a result of the purification of the nucleoli and the production of monoclonal antibody reagents. A number of these proteins, from amphibians, mammals, and Physarum, have $M_r$ values between 34,000 and 40,000. The abundant phosphoprotein B23 ($M_r$=37,000), NO38 ($M_r$=38,000), and ribocharin ($M_r$=40,000), occur in the granular component (Hügle, B., et al. (1985) Cell. 41:615–627; Schmidt-Zachmann, M. S. et al. (1987) EMBO (Eur. Mol. Biol. Organ) J. 6:1881–1890; and Spector, D. L., et al. (1984) Chromosoma (Berl.) 90:139–148). Recently, the primary structure of NO38 was determined (Schmidt-Zachmann, et al. (1987) Supra). Fibrillarin ($M_r$=34,000) is located within the fibrillar component. Interestingly, fibrillarin was identified with a serum from a patient with the autoimmune disease scleroderma, and appears to have a wide-spread distribution in nature as assayed by immunoblot (Lischwe, M. A., et al. (1985) J. Biol. Chem. 260:14304–14310 and Osch, R. L., et al. (1985) Biol. Cell 54:123–134). Protein B-36 ($M_r$=34,000), and a polypeptide constituent ($M_r$=38,000), among others, of a nucleolar martrix, have also been identified (Christensen, M. E., et al. (1986) Exp. Cell Res. 166:77–93; Fields, A. P., et al. (1986) Exp. Cell Res. 164:139–153; and Kistler, J., et al. (1984) J. Cell Biol. 99:1981–1988). Certain nucleolar antigens within this molecular weight range, such as cyclin and P40, are preferentially expressed in association with rapid cell proliferation (Celis, J. E., et al. (1985) Proc. Natl. Acad. Sci. USA 82:3262–3266 and Chatterjee, A., et al. (1987) Cancer Res. 47:1123–1129). A number of other nucleolar proteins have also been studied (Fakan, S., et al. (1986) Biol. Cell. 56:189–206; Goessens, G., et al. (1984) Supra; Hadjiolov, A. A. (1985) Supra; and Jordan, G. (1987) Nature (Lond.) 329:489–490).

Although a large amount is understood concerning the proteins that contribute to the three morphological subdivisions of the nucleolus, much less detail is available concerning the function(s) of the respective proteins. Recent in vivo studies have examined the process of nucleolus reassembly after mitosis (Benavente, R., et al. (1987) J. Cell Biol. 105:1483–1491). To gain more insight into the function, a series of monoclonal anti-bodies have been produced which are specific for the nucleolus of the budding yeast S. Cerevisiae. Three of these monoclonal antibodies which react with a protein of $M_r$=38,000, are disclosed herein. This is the first teaching which identifies a protein specifically localized within the nucleolus in yeast, and suggests that the study of nucleolar function in yeast will extend to higher cell types.

EXAMPLE 1
Yeast Strains, Reagents, and Materials

The protease-deficient, haploid Saccharomyces cerevisiae strain BJ2168 (a, trp1, leu2, ura3-52, prb1-1122, pep4–3, prcl-407) was obtained from the Yeast Genetic Stock Center, University of California, Berkeley, Calif. The standard Fleischmann's yeast strain was purchased at Sloan's Supermarket, New York. Buffalo rat liver (BRL) cells were from the American Type Culture Collection, Rockville, Md. Lyticase, phenylmethylsulfonyl fluoride (PMSF), bovine serum albumin (BSA), DNase I (type DN-EP), RNase A (type III), and 4',6-diamidino-2-phenylindole (DAPI) were from Sigma Chemical Co., St. Louis, Mo. DL-Dithiothreitol (DTT), TRITON X-100. (Triton registered trademark of Union Carbide Co. for synthetic organic composition, micrococcal nuclease, and affinity-purified rabbit anti-mouse 10-nm colloidal gold were obtained from Boehringer Mannheim Biochemicals, Indianapolis, Ind. Ultrapure TX-100 used in IEF and nonequilibrium pH gradient electrophoresis (NEPHGE) gels was from Pierce Chemical Co., Rockford, Ill. Fluorescein-conjugated and unconjugated, affinity-purified rabbit anti-mouse IgG antibody were from Cooper Biomedical, Inc., Malvern, Pa. $^{125}$I-protein A ($\mu$=micro) (2–10 $\mu$Ci/$\mu$g) was from DuPont NEN Research Products, Wilmington, Del. Paraformaldehyde (EM grade), glutaraldehyde (EM grade), polylysine hydrobromide, LR White embedding resin, tannic acid, and uranyl acetate were from Polysciences, Inc., Warrington, Pa. Resin LX-112 was from Ladd Research Industries, Burlington, Vt. Sodium dodecyl sulfate (SDS) was obtained from BDH Chemicals Ltd., Dagenham, Essex, UK. Ficoll 400 was from Pharmacia Fine Chemicals, Piscataway, N.J. Ampholines were from LKD Instruments, Inc., Gaithersburg, Md. All other chemicals, reagents, and media components were obtained from customary scientific vendors and were of high purity.

EXAMPLE 2
Purification of Nuclei

Strain BJ2168 was grown in 12 liters of 1% yeast extract, 2% peptone, 2% dextrose (YPD medium) supplemented with tryptophan and uracil (25 $\mu$g/ml) at 30° C. to a value of $A_{600}$=1. The yeast cultures were chilled to about 10° C. by the addition of ice and collected by concentration with a pellicon cassette system (Millipore, Bedford, Mass.), followed by centrifugation in a GS3 rotor (Sorvall Instruments, Newton, Conn.) at 4,200 g (maximum) (5,000 rpm) for 5 min. The yeast were washed once with 5 pellet volumes of cold spheroplasting medium (1M sorbitol, 2% dextrose, 0.2% yeast nitrogen base, 0.2% casein amino acids, 100 mM Hepes acid, 50 mM Tris base), and the pellets weighed. About 18 $\mu$g of yeast were resuspended with approximately 9 vol (160 ml) of spheroplasting medium containing 2 mM DTT and 4 mg Lyticase per 1 $\mu$g cells (wet weight). The yeast were digested for 1 h at 30° C. with frequent stirring. During the digestion the pH decreased from 8 to 6. For the first 30 min the pH remained in the optimum range for removal of the cell wall by Lyticase. During the final 30 min the spheroplasts grew actively, acidified the medium, and "recovered" from the digestion. The remainder of the procedure, except the homogenization step, was done at 0°–5° C. The spheroplasts were chilled on ice, centrifuged through a cushion (0.6M sorbitol, 0.6M sucrose, 2% wt/vol Ficoll 400, 20 mM MES-Tris, pH 6.5) for 6 min at 4,300 g (maximum) (6,000 rpm) in a Sorvall SS-34 rotor, and washed once (1.2M sorbitol, 2% Ficoll 400,20 mM MES-Tris, pH 6.5). The wash buffer and all subsequent buffers contained protease inhibitors (1 mM epsilon-aminocaproic acid, 5 $\mu$g/ml aprotinin, 1 mM p-aminobenzamidine, 1 $\mu$g/ml chymostatin, 5 $\mu$g/ml pepstatin, 250 $\mu$ M PMSF, 50 $\mu$M p-chloromercuriphenyl sulfonic acid). Spheroplasts were resuspended in 180 ml of lysis buffer (20% Ficoll 400, 20 mM $KP_i$, pH 6.5, 1 mM $MgCl_2$) at 20° C. and Dounce homogenized with 15 strokes using a loose fitting ("B") pestle. The lysate was chilled completely on ice and centrifuged for 5 min at 13,400 g (maximum) (9,000 rpm) in a Sorvall HB-4 rotor. The supernatant was transferred to another tube and centrifuged as before for 10 min. The supernatant was carefully transferred to six SW28 tubes (Beckmann Instruments, Inc., Fullerton, Calif.) previously filled with a three-step gradient of 30, 40, and 50% Ficoll 400 in the same buffer (5 ml each step). The gradients were centrifuged at 58,400 g (maximum) (18,000 rpm) in a Beckmann SW28 rotor for 1 h at 4° C. After centrifugation, the 40% Ficoll layer was collected along with some of the 30 and 50% layers. For further purification, the nuclei were diluted with 1 vol of buffer and separated with another step gradient in two SW28 tubes. The nuclei, typically at a protein concentration of 4 mg/ml, were stored at −80° C. in suspension as collected from the step gradient. Rat liver nuclei were purified according to Blobel and Potter (Blobel, G., et al. (1966) Science (Wash. D.C.) 154:1662–1665). Nuclei from *Neurospora crassa* were prepared as described above for *S. cerevisiae*, from the cell wall-less fz, sg, os-1 strain grown in liquid culture to $A_{600}=1$ using standard techniques.

EXAMPLE 3
Digestion and Extraction of Nuclei

DNase I and RNase A digestions, and extractions with salt, or urea, or detergent were done in SPDM buffer: 250 mM sucrose, 20 mM $KP_i$, pH 6.5, 1 mM DTT, 0.1 mM $MgCl_2$. Protease inhibitors were present at one-fifth the final concentration used for the isolation of nuclei. All operations were done in the cold except where noted. Typically, 100 μl (approximately 400 μg protein) of nuclei suspended in the Ficoll buffer were diluted with 900 μl of SPDM buffer and centrifuged in a Beckman TLA 100.2 rotor at 10,300 g (average) (17,000 rpm) for 10 min. The pellet was resuspended by homogenization in 0.5 ml SPDM buffer. DNase I and/or RNase A were added (4 μl of a 10 mg/ml solution in PBS plus 50% glycerol and 1 mM $MgCl_2$), and the mixture was placed at 20° C. for 10 min. EDTA was then added to a final concentration of 1 mM, followed by homogenization, and 5 min at 20° C. The digestion mixture was chilled and nuclear envelopes were collected by centrifugation as above. For extractions, nuclear envelopes were resuspended by homogenization in a volume of SPDM buffer that gave a final volume of 0.5 ml after extraction. Extraction with salt was done by adding an equal volume of 2M NaCl in SPDM buffer without sucrose. Extraction with urea was done by adding 2 vol of 9M urea in buffer without sucrose. Triton X-100 was added to 1% from a 20% (wt/vol) stock. The extractions were done for 10 min on ice, after brief homogenization. The samples were centrifuged as above in a Beckman TLA 100.2 rotor and prepared for SDS-PAGE.

Samples for IEF and NEPHGE gels were prepared as follows. Nuclei (approximately 100 μg protein) were diluted in 1 ml of 250 mM sucrose, 25 mM Tris HCl, pH 8.8, 1 mM DTT, 0.1 mM $MgCl_2$, 0.1 mM $CaCl_2$. Sonication with a Microtip sonifier (Branson Sonic Power Co., Danbury, Conn.) was done for 1 min without heating, and 1 μl of micrococcal nuclease (10 mg/ml solution in PBS plus 50% glycerol and 1 mM $MgCl_2$) was added. After incubation performed as described above, the samples were precipitated with 10% TCA, washed with 0.5% TCA and solubilized for IEF or NEPHGE.

EXAMPLE 4
Monoclonal Antibody Production

Purified nuclei in native form were prepared for immunization by diluting a Ficoll suspension of nuclei 10 fold with 20 mM $KP_i$, 1 mM $MgCl_2$, and centrifuging in an Eppendorf microfuge at 10,000 g for 10 min in the cold. The nuclei were resuspended in 10 μl of sterile PBS with 1 mM $MgCl_2$, and emulsified with an equal volume of Freund's adjuvant. A 2-month old female BALB/c mouse was immunized intraperitoneally with 100 μg of native nuclei in complete adjuvant, and boosted 4–6 wk later with 100 μg of antigen prepared in the same way in incomplete adjuvant. This procedure was repeated for about 6 mo. The final boosts consisted of two intravenous injections of 400 μg of antigen given at 3 d and 1 d before the mouse was sacrificed. Spleen cells were fused with NS-1 myeloma cells and selected hybridomas cloned according to established methods as described (Davis, L. I., et al. (1986) Cell. 45:699–709, Siraganian, R. P., et al. (1983) Methods Enzymol. 92:17–26; and Stahl, C., et al. (1983) Methods Enzymol. 92:26–36).

EXAMPLE 5
SDS-PAGE, Immunoblotting and Two Dimensional Gel Electrophoresis

SDS-Page was carried out with 10.5% slab gels as described by Laemmli (Laemmli, U. K. (1970) Nature (Lond.) 227:680–685), with the addition of 10% sucrose to the stacking gel. Protein samples were solubilized with bath sonication, but without heating, in a sample buffer solution of 4% SDS, 100 mM DTT, 15% glycerol, 0.5M Tris base, and 0.02% bromophenol blue dye. Samples collected as pellets were solubilized directly in sample buffer. Supernatants were precipitated with TCA. Supernatants containing 1M NaCl or 6M urea were treated with 2 vol of 30% (wt/vol) TCA. Precipitates containing TX-100 were washed with cold acetone.

For immunoblotting, proteins were electrophoretically transferred to nitrocellulose essentially according to Towbin et al. (Towbin, H., et al. (1979) Proc. Natl. Acad. Sci. USA 76:4350–4354). The nitrocellulose membrane was air dried, and all subsequent procedures were done at room temperature using a standard buffer consisting of PBS, 0.1% TX-100, and 0.01% SDS. The membranes were blocked with 3% BSA in the standard buffer. Monoclonal supernatants, diluted 1 in 5 with the standard buffer containing 1% BSA and 2 mM $NaN_3$, were incubated with the nitrocellulose membrane(s), for 1–2 h. Affinity-purified rabbit anti-mouse IgG antibody diluted 1:1,000 in the standard buffer plus 1% BSA was incubated as above for the second step. $^{125}$I-protein A diluted 1:2,000 was used as the final step in the same buffer. Washes between steps were done with the standard buffer for 5 min, four times. Dried nitrocellulose membranes were exposed at −80° C. with Picker x-ray film in cassettes equipped with intensifying screens.

First dimension IEF and NEPHGE tube gels were run according to standard methods using 9M urea, 1% ultrapure TX-100 detergent, and 2% ampholines, in 4% polyacrylamide (O'Farrel, P. H. (1975) J. Biol. Chem. 250:4007–4021 and O'Farrel, P. Z., et al. (1977) Cell. 12:1133–1142). The second dimension was done using 10.5% SDS-PAGE.

EXAMPLE 6
Immunofluorescence Microscopy and Election Microscopy

A standard Fleischmann's yeast strain and strain BJ2168 were used with the following modifications of standard methods for immunofluorescence (Kilmartin, J. V., et al. (1984) J. Cell Biol. 98:922–933). All steps were performed at room temperature unless noted otherwise. For one slide, 10 ml of yeast in YPD medium were grown to an $A_{600}=1$ and chilled on ice. After collection by centrifugation, the yeast were washed two times with cold 25 mM $NaP_i$, pH 6.8. Fixative was prepared by vortexing 2 μg paraformaldehyde powder into 5 ml of water. The suspension was carefully heated on a flame to boiling with intermittent vortexing. While hot, 100 μl of 1M NaOH was added slowly with vortexing (most but not all of the solid dissolves). The fixative was diluted 10-fold with the phosphate buffer to give approximately 3% formaldehyde. Glutaraldehyde, when used in combination with formaldehyde, was diluted from a 25% stock to 0.1%. The yeast were fixed for 30 min on ice, followed by 60 min at room temperature. Fixed yeast were washed once with the phosphate buffer, once with the same buffer plus 50 mM $NH_4Cl$, and once again with the phosphate buffer. To remove the cell wall, the yeast were resuspended in 100 1 of 1M sorbitol, 2 mM DTT, 1 mg/ml Lyticase, 25 mM $NaP_i$, pH 6.8, and digested for 30 min.

Yeast fixed with glutaraldehyde were digested for 1 h. Digested yeast were washed twice with the phosphate-sorbitol buffer, once with a 1:1 mixture of phosphate-sorbitol buffer/PBS plus 1 mM $MgCl_2$ (PBS/Mg), and once with PBS/Mg. The yeast were resuspended in PBS/Mg with protease inhibitors and allowed to settle onto polylysine coated, eight chamber slides (Titertek, Elfab Oy, Finland) overnight at 4° C. (1 ml of 0.002% polylysine was previously dried onto each slide). The slides were washed once with PBS/Mg and the cells were permeabilized using MeOH at −20° C. for min., followed by three washes with PBS/Mg. TX-100 (0.1%) in PBS/Mg was applied for 5 min. followed by three PBS/Mg washes. BSA (1%) in PBS/Mg was used to block binding sites and undiluted hybridoma supernatant was added, and incubated 1 h. For immunofluorescence, the supernatants were neutralized by adding 1M Hepes acid to 40 mM. Five washes were done with 0.1% BSA in PBS/Mg for 5 min each. Affinity-purified fluorescein-conjugated rabbit anti-mouse antibody (preadsorbed with fixed, digested, permeabilized, and blocked yeast cells) was diluted 1 in 10 with 1% BSA in PBS/Mg and incubated with the samples for 1 h. The samples were washed as above, air dried, and mounted with 1 mg/ml p-phenylenediamine in 90% glycerol, 10% Tris-buffered saline, pH 8.0 containing 0.1 $\mu$g/ml DAPI. Immunofluorescence microscopy of BRL cells was performed on monolayers grown on multiwell slides, using standard conditions for pretreatment, fixation, permeabilization, and antibody binding (Davis, L. I., et al. (1986) Cell 45:699–709). Specimens were observed with a Zeiss Photomicroscope III using 40× and 10× planapochromat and plan neofluar objectives, and images recorded with Kodak T-MAX film, ASA 400.

For routine examination of samples for purposes of ascertaining purity or composition, conventional methods were used for fixation with glutaraldehyde, postfixation with osmium tetroxide, embedding in LX-112 resin, ultrathin sectioning, and staining (Davis, L. I., et al. (1986) Supra). For immunolocalization electron microscopy, nuclei were embedded in the hydrophilic resin LR White as follows. Purified nuclei were fixed in suspension with a 10-fold dilution using freshly made 3% formaldehyde, 0.1% glutaraldehyde, 0.1% picric acid, 0.01% tannic acid, 50 mM $KP_i$, pH 6.5,5 mM $MgCl_2$ for 1 h at 0° C. The nuclei were diluted with 50 mM $KP_i$, pH 6.5,5 mM $MgCl_2$, centrifuged in a Eppendorf microfuge 10 min in the cold, and washed three times with the same buffer. The sample pellets were dehydrated in 5-min steps using 70, 90, and 100% (twice) ethanol. LR white was added, and the pellet dislodged and sealed airtight in a Beem capsule containing fresh LR white. The resin was polymerized by baking at 60° C. for 24 h. Thin sections on 300 mesh copper grids were incubated successively for 10 min in water, 15 min in 1% BSA in PBS/Mg, and 1 h in undiluted hybridoma supernatant. After three 5-min washes in 0.1% BSA in PBS/Mg, the grids were incubated in a suspension of 10 nm colloidal gold coated with rabbit anti-mouse antibody diluted 1 in 20 with 1% BSA in PBS/Mg for 1 h. The grids were washed as above, washed in water for 1 min three times, and stained with freshly prepared 1% aqueous uranyl acetate for 5 min. The grids were washed for 1 min 5 times with water and placed in lead stain for 3 min. Lead stain was made by diluting Reynolds lead 1 in 10 with 10 mM NaOH (Reynolds, E. S. (1963) J. Cell Biol. 17:208–212). The grids were washed for 1 min in 10 mM NaOH three times, followed by three water washes. Specimens were visualized with a JEOL 100CX electron microscope at 60 kV, and photographs were recorded with Kodak electron microscope film.

EXAMPLE 7

Purification of Yeast Nuclei

Yeast nuclei were purified using a modification of the methods of Mann and Mecke, and Ruggieri and Magni (Mann, K., et al. (1980) FEBS (Fed. Eur. Biochem. Soc.) Lett. 122:95–99 and Ruggieri, S. (1982) Physiol. Chem. Phys. 14:315–322). The protease deficient yeast strain BJ2168 was used to reduce proteolytic degradation of nuclei. A protease inhibitor cocktail was also used to reduce the activity of nuclear proteases (Ruggieri, S. (1982) Supra). Lyticase was used to digest yeast cell wall instead of zymolyase because of its reduced content of DNase and RNase activities (Scott, J. H., et al. (1980) J. Bacteriol. 142:414–423). As a precaution against in vitro artifacts, our method maintains cells in a medium that supports growth during and after the removal of the cell wall. We found that yield and purity of nuclei were affected by various conditions. The following conditions resulted in poor hypotonic lysis of spheroplasts and low nuclei yield: lysis buffer (see Examples 1–6 for Materials and Methods) including $Mgcl_2$, or spermine, or spermidine, at 5 mM; inclusion of 50 mM NaCl or KCl in the Ficoll-containing buffers; lysis at low temperature (0°–5° C.). Ficoll-containing buffers of pH 7.5 or 8.5, or a $MgCl_2$ concentration of 0.1 mM reduced the structural integrity and purity of nuclei. The use of a step gradient reduced contamination of nuclei by unlysed spheroplasts and cell wall fragments, which pellet below the step gradient. The Ficoll gradient separation will be discussed in greater detail in conjunction with FIG. 3, which shows the presence of p38 in different subcellular fractions. It is noted that this method is equally applicable to the purification of nuclei from *Neurospora crassa*.

Figure 1B:
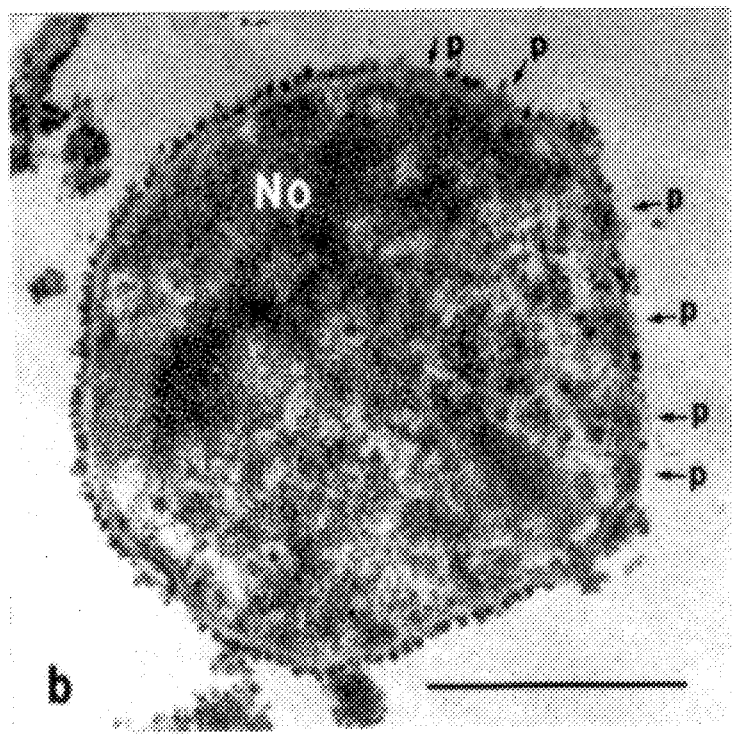

Nuclei prepared with two Ficoll gradient steps are highly purified, with the main contaminating material being membranes (FIG. 1a). The nuclei are approximately 1 micron in diameter and exhibit the characteristic envelope with associated ribosomes and pore complexes (FIG. 1b). An intact endoplasmic reticulum cisturnum was often attached to the envelope. The nucleolus is evident as a densely staining "crescent," which does not show the ultrastructural heterogeneity observed in higher eucaryotic cells, when viewed at high magnification (FIG. 1b).

EXAMPLE 8

Three Monoclonal Antibodies Directed against a 38,000 Molecular Weight Protein

Figure 2:
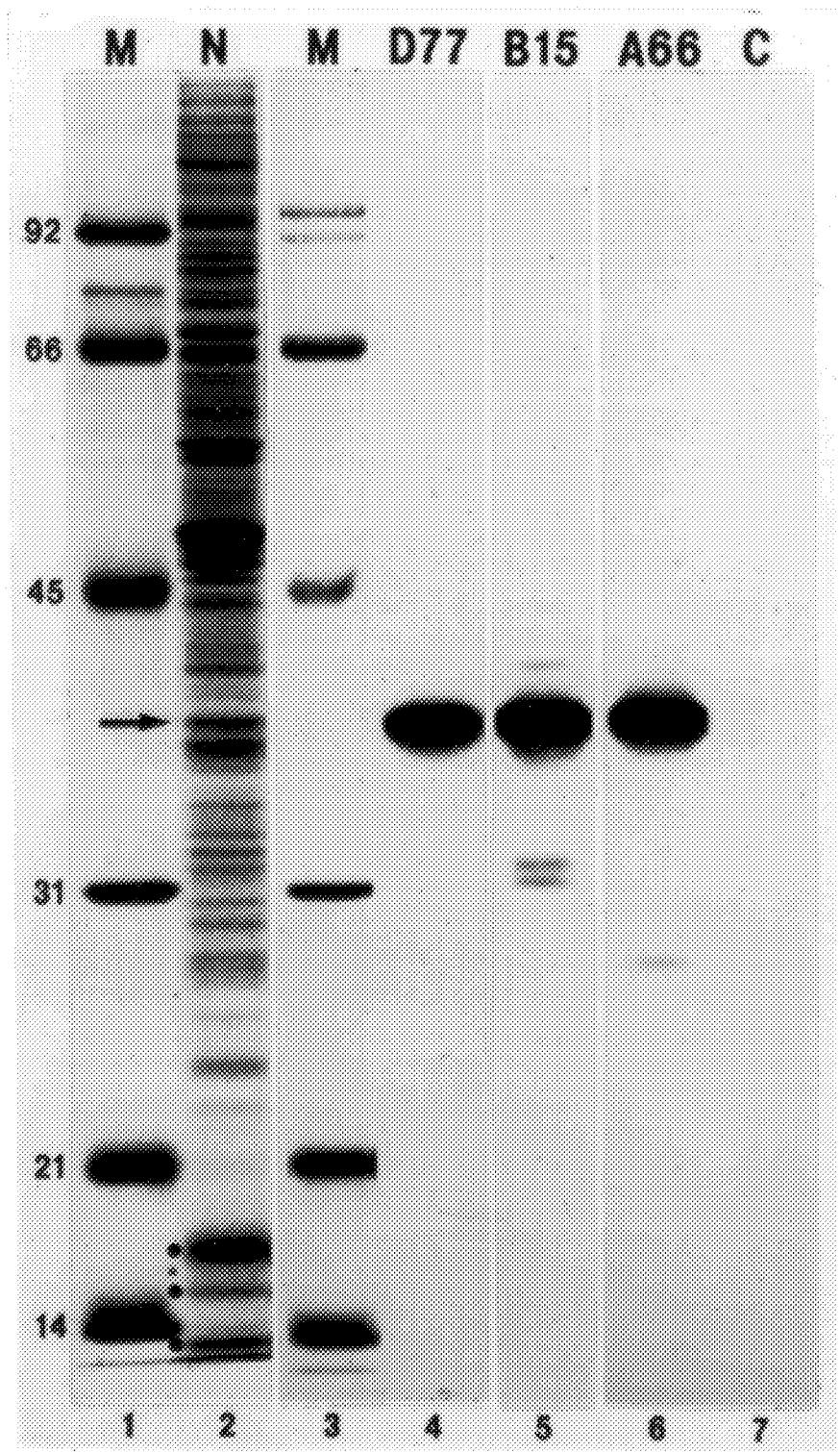
FIG. 2. Monoclonal antibodies specific for a 38,000-mol wt protein. Yeast nuclear proteins (100 µg) were separated by 10.5% SDS-PAGE and stained with Coomassie Blue (lane 2) or probed by immunoblotting (lanes 4–7). Immunoblots incubated with the monoclonals D77, B15, and A66, followed by $^{125}$I-protein A and autoradiography, demonstrate binding to a protein of $M_r$ 38,000, whereas a control culture medium (C) does not. Among the proteins of the nuclear sample (N) are a 38,000-mol-wt protein (arrow) and histones (solid circles). Protein molecular weight standards (M) are shown with approximate values ($M_r \times 10^{-3}$) (lane 1). [$^{14}$C] Protein standards on the immunoblot were exposed after fluorography (lane 3). The immunoblots were exposed to film for different lengths of time.

Purified nuclei were used to immunize mice, and monoclonal antibodies were prepared using standard methods. Three different monoclonals reacted on immunoblots with a protein of apparent molecular weight 38,000 by SDS-PAGE (FIG. 2). This protein is referred to as p38. Monoclonal D77 possesses the highest specificity for p38, and does not show cross-reactivity with any other protein even after long exposure of the immunoblot. Monoclonals B15 and A66 detect p38, but bind with low affinity to four other proteins of $M_r$ 41,000, 31,000, 32,000, and 28,000 respectively (FIG. 2). Brief exposure of the immunoblots of each of the monoclonals showed two closely migrating protein bands at 38,000, the lower one of which was markedly fainter. The protein p38 may be identified in a Coomassie Blue stained protein profile of nuclei (FIG. 2). Note that the yeast histones are prominent among the nuclear proteins.

Protein p38 Occurs Predominantly in the Subcellular Fraction Containing Pure Nuclei.

The Ficoll 400 step gradient was prepared by loading a spheroplast lysate in 20% Ficoll over three layers of 30, 40, and 50% Ficoll (see Examples 1–6 for Materials and Methods). After centrifugation, four fractions were collected to obtain a representative cross section of all proteins present in the spheroplast lysate. These are low density membranes (L), soluble components (S), high density membranes (H), and nuclei (N). The L fraction was collected as a band of membranes that floated to the top of the 20% Ficoll layer. Below the L band was the 20% Ficoll layer that contained soluble cell components. A band that occurred at the interface between the 20 and 30% Ficoll layers was enriched in higher density membranes such as endoplasmic reticulum. Nuclei were collected from the 40% layer. Equal amounts of protein from each of these fractions are compared by a Coomassie Blue stained gel (FIG. 3a). Two indications of the purity of the nuclear fraction are the enrichment of histones in this fraction, and the lack of the low molecular weight ribosomal proteins (FIG. 3a).

The protein p38 occurs almost exclusively in the nuclear fraction. This is evident from the immunoblot analysis and the Coomassie Blue staining of the four subcellular fractions (FIG. 3). The D77 epitope is found exclusively in the nucleus (FIG. 3b). Longer exposure times did not show D77 bound to any nonnuclear p38 species. B15 detects a minute amount of p38 in the H fraction (FIG. 3c). Monoclonal A66 reveals a small, but significant, amount of p38 in the L and H fractions (FIG. 3d). The small quantities of p38 in the L and H fractions are visible as faint bands stained by Coomassie Blue (FIG. 3a). None of these three monoclonals reacted with other yeast proteins. Virtually all of the proteins present in the crude spheroplast lysate are represented in the combination of fractions L, S, H, and N. As a control, we include the results using monoclonal C56, which shows the distribution of a $M_r$ 98,000 protein located in the L and H fractions (FIG. 3e). Monoclonal C56 was specifically selected during the preparation of antibodies as a control marker for a nonnuclear protein. The 98,000 molecular weight protein is exclusively localized to the plasma membrane.

Fraction of Yeast Nuclei and the Disposition of p38

Figure 4A:
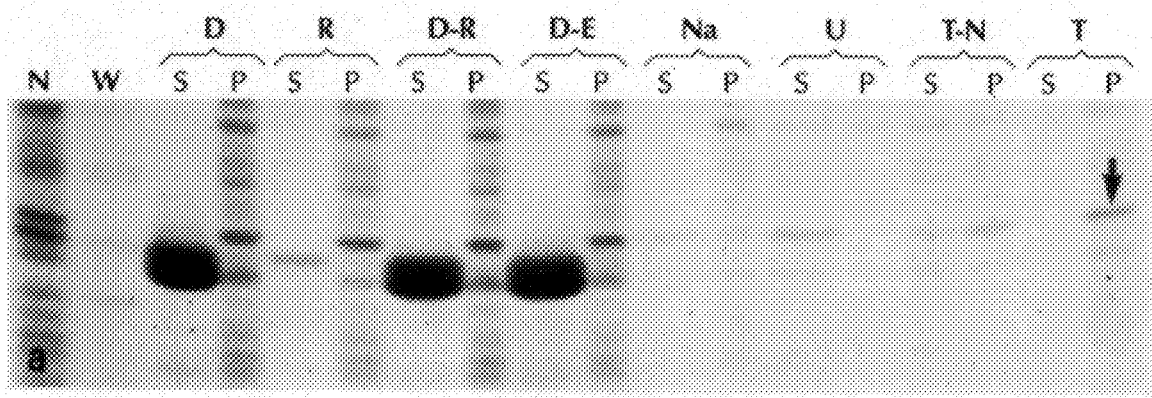
FIGS. 4(a), 4(b) and 4(c) depict the subfractionation of purified nuclei. Nuclei were digested and extracted with various reagents, subject to 10.5% SDS-PAGE, and analyzed with Coomassie Blue staining (a), silver staining (b), or immunoblotting with the D77 monoclonal and autoradiography (c). Nuclei (N, 50 µg protein) were washed with buffer containing a low concentration of $MgCl_2$ (0.1 mM) to give a wash supernatant (W). Digestions with DNase (D), or RNase (R), or DNase and RNase(D-R), or DNase followed by an EDTA extraction (D-E) were performed, followed by centrifugation to give supernatant (S) and pellet (P) fractions. Nuclear envelopes (D-E pellet) were extracted with 1M NaCl(Na), or 6M urea (U), or 1% TRITON X-100 (a nonionic surfactant) plus 0.1M NaCl (T-N), or 1% TRITON X-100 (T), and centrifuged. Protein p38 is indicated by arrows. DNase is the prominent band in the supernatant fraction.
Figure 4B:
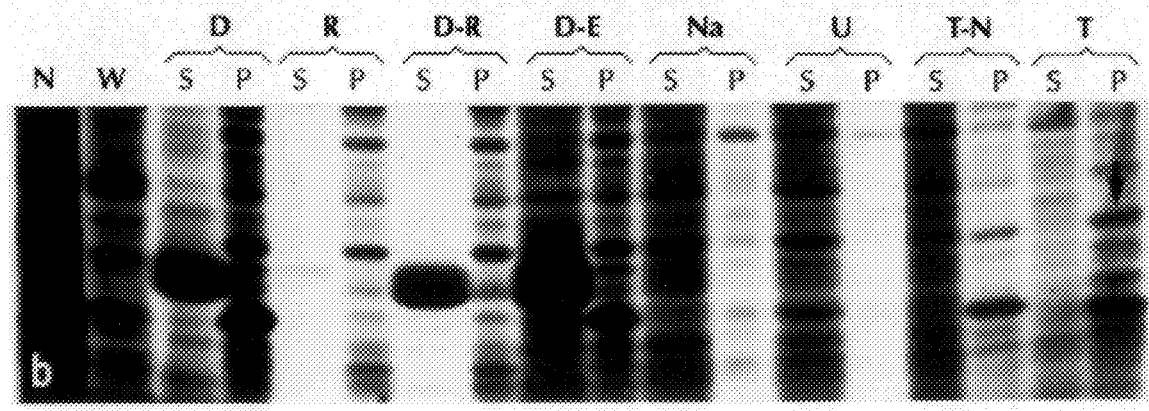
Figure 4C:
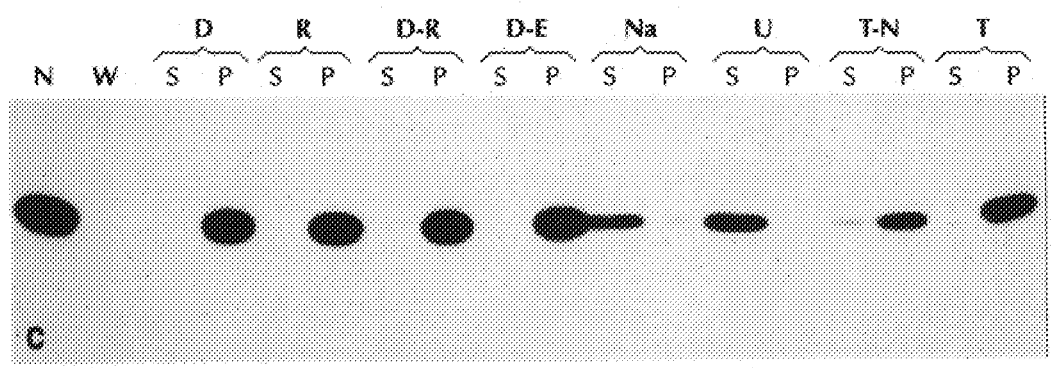

To investigate some of the intranuclear interactions in which p38 participates, nuclei were digested with DNase and/or RNase, nuclear envelopes were extracted with NaCl, or urea, or the nonionic detergent Triton X-100 (see Examples 1–6). For these experiments, nuclei were washed with a buffer containing a low concentration (0.1 mM) of $MgCl_2$. This resulted in "uncoiling" of the chromatin and nucleolar regions within the nucleus, as indicated by an increase in nuclear size and a reduction in staining intensity observed by electron microscopy. DNase and RNase, used alone or together, do not release p38 from the nucleus (FIG. 4). In general, very few proteins are removed by nuclease digestions. To prepare envelopes, the DNase digestion was followed with a brief extraction with EDTA, which removed more protein and caused the release of approximately 80% of the histones. Envelopes prepared in this fashion are shortened double membrane sheets with intranuclear material attached, and studded with ribosomes on the exterior.

Nuclear envelopes were extracted under the following conditions: 1M NaCl, or 6M urea, or 1% TX-100+0.1M NaCl, or 1% TX-100. High concentrations of NaCl and urea remove p38 from envelopes (FIG. 4). The same effect was observed with 0.5M NaCl, or 1M KC1. Detergent seemed to have a minimal effect, removing only a small amount of p38 in the presence of 0.1M NaCl (FIG. 4). Electron microscopy of 1M NaCl washed envelopes showed that the intranuclear material and ribosomes were removed completely, leaving membranes interrupted with "residual" pores.

Since p38 is not released from nuclei with DNase and/or RNase, this suggests that p38 is not loosely bound to DNA or RNA, and may be associated with other nuclear proteins. These interactions are interrupted by the relatively harsh treatments that strip the majority of proteins from envelope membranes. Consistent with the behavior of other nucleolar proteins, p38 does not appear to be an integral membrane protein.

Immunofluorescent Localization of p38 in Growing Yeast Cells

Figure 5:
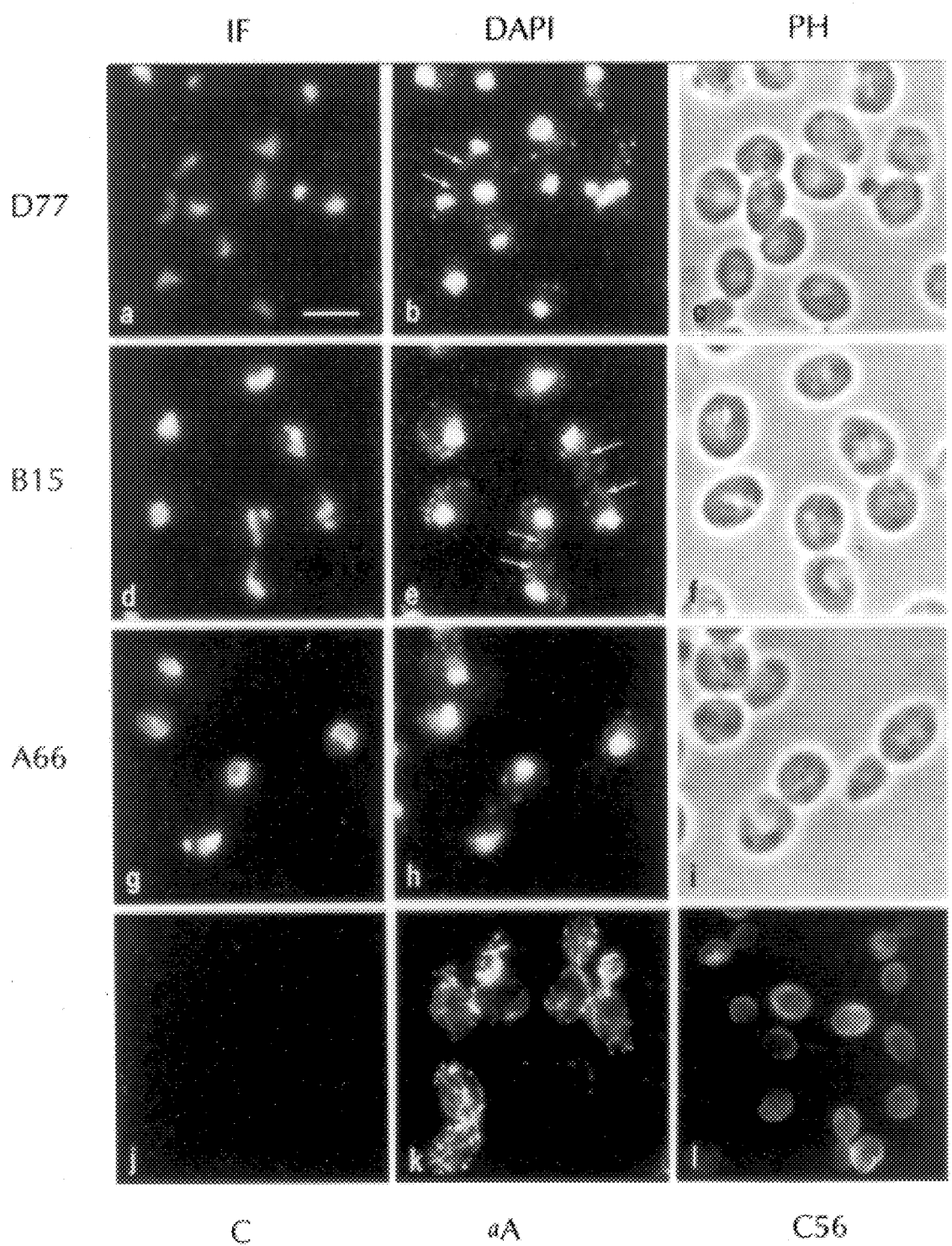
FIGS. 5(a) through 5(l) show immunofluorescence localization of p38 in yeast. Immunofluorescence was done with Fleischmann's yeast, using a fluorescein-conjugated antimouse secondary reagent, and samples were prepared for microscopy using standard methods. Immunofluorescence micrographs (a, d, g), with the corresponding DAPI (4'-6-diamidino-2-phenylindole) counter staining of chromatin (b, e, h) and phase contrast (c, f, i) views, show the results with the monoclonals D77, B15, and A66. Chromatin extending into the bud neck may be seen in mitotic cells (arrows). For comparison, immunofluorescence results with a control hybridoma supernatant (C), an anti-yeast actin antibody (A), and the monoclonal C56 using yeast strain BJ2168, are shown (j-1). Bar, 2 µm.

Indirect immunofluorescence was done on whole yeast cells to further define the intracellular distribution of p38. A Fleischmann's yeast strain was used for this purpose instead of strain BJ2168 because of the larger cell and nuclear size, and the presence of more mitotic pairs. All three monoclonals directed against p38 produce a "crescent" shaped immunofluorescence pattern, that was also localized to the region between dividing pairs of cells (FIG. 5). DAPI counter staining, indicating the distribution of chromatin (and mitochondria), and phase contrast views for each immunofluorescence result are shown. It is noted that the spheroplasting enzyme lyticase gave more intense DAPI staining of nuclei than zymolyase in this procedure, suggesting that lyticase may be superior to zymolyase for immunofluorescence experiments.

The monoclonal D77 gives the faintest signal, and fewer dividing pairs had fluorescence through the bud neck (FIG. 5a). Monoclonal B15 gives an intermediate staining intensity, and A66 produced the brightest fluorescence signal (FIG. 5, d and g). Both B15 and A66 give more frequent fluorescence staining through the bud neck. The pattern of fluorescence with the three monoclonals suggests that p38 has a crescent-shaped distribution around a central chromatin mass during interphase. Mitosis produces a more "patchy" distribution of p38, which extends to different degrees into the daughter cell. Unlike D77 and B15, A66 gives a "rim" staining pattern in most of the nucleoli (FIG. 5g). Identical results to those obtained with the Fleischmann's yeast strain were obtained with strain BJ2168.

The ultrastructure of the yeast cells prepared for immunofluorescence is well preserved. Actin cables and cortical spots are retained (FIG. 5k). The plasma membrane organization is intact, as shown by the distribution of the 98,000 molecular weight protein detected by monoclonal C56 (FIG. 5l). In addition, antibody to β-tubulin decorated the characteristic microtubules that extend between spindle plaques of mitotic nuclei. Interestingly, the binding of D77 to p38 is eliminated if yeast cells are fixed with glutaraldehyde, even at low concentration (0.1%). However, both B15 and A66 retain the ability to recognize p38 in yeast cells fixed with this concentration of glutaraldehyde.

Figure 6A:
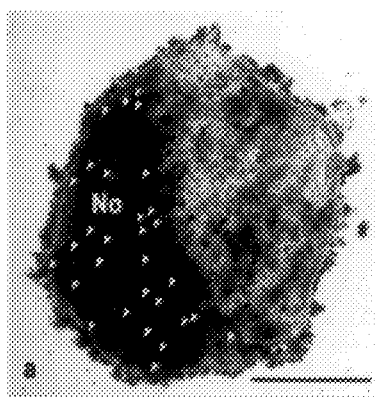
FIGS. 6(a) though 6(c) shows immunolocalization electron microscopy of p38 to the nucleolus. Ultrathin sections of nuclei embedded in LR White were incubated with the monoclonals A66 (a) and B15(b) followed by secondary antibody adsorbed to 10 nm colloidal gold, and stained for electron microscopy. Essentially all of the p38 localized by the colloidal gold (arrowheads) occurs in the nucleolus (No). The control culture medium shows no decoration of the nucleolus (c). Bar, 0.5 µm.
Figure 6B:
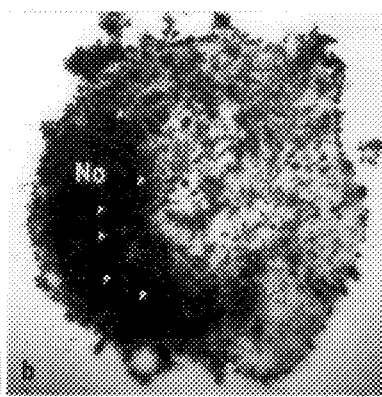
Figure 6C:
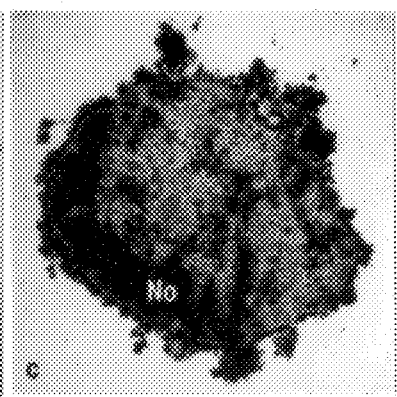

Postembedding Immunoelectron Microscopy of Yeast Nuclei Localizes p38 to the Nucleolus The "crescent" fluorescence pattern strongly suggested staining of the nucleolus. To confirm the intranuclear location of p38, and to show labeling of the dense crescent precisely, postembedding immunogold labeling was performed. Purified nuclei were fixed with formaldehyde and glutaraldehyde and embedded in the hydrophilic resin LR White as described in Examples 1–6 of Materials and Methods. No osmium tetroxide postfixation was performed. Ultrathin sections were incubated with the monoclonals, then colloidal gold secondary reagent, and stained with standard uranium acetate and Reynolds lead preparations. Monoclonal A66 clearly decorates the nucleolar crescent (FIG. 6a). The nucleolus is also labeled by B15, but more weakly (FIG. 6b). Glutaraldehyde fixation destroyed the D77 epitope, as mentioned above, and resulted in no gold particles attached to the nucleolus. Only a minimum number of gold particles bind to the nucleolus in the absence of the monoclonal antibodies (FIG. 6c). The decoration shows with colloidal gold appears uniform, suggesting that p38 is evenly distributed throughout the nucleolus. It is difficult to determine whether or not fibrils within the nucleolus are labeled because of heavy accumulation of stain by the nucleolus.

EXAMPLE 9

Immunologic Cross-reactivity between p38 and Proteins in Purified Nuclei from Rat Liver and *Neurospora crassa*

Figure 7:
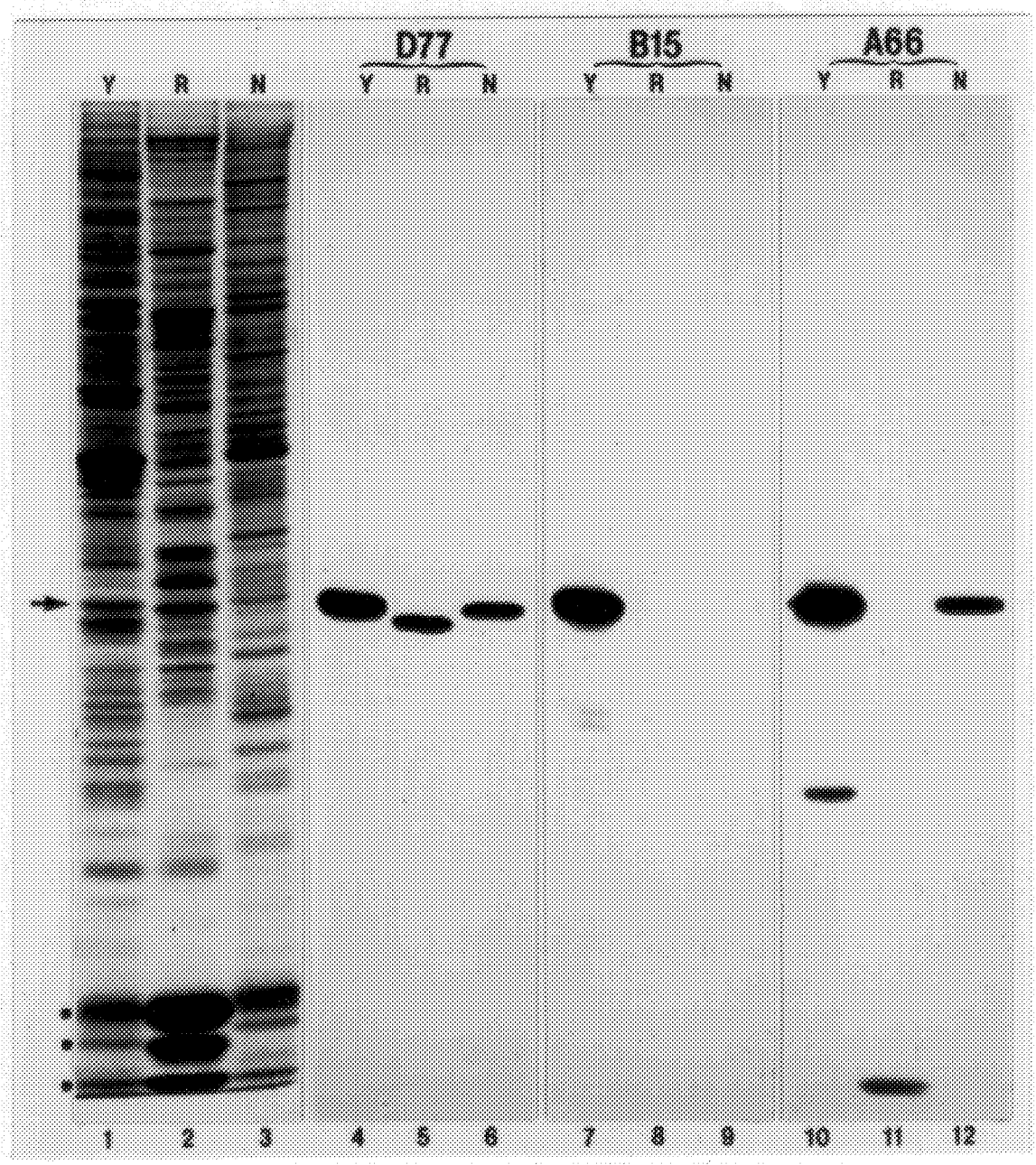
FIG. 7. Proteins cross-reacting with p38 from rat liver and Neurospora crassa. Purified nuclei (100 µg protein) from yeast (Y), rat liver (R), or N. crassa (N) were subjected to 10.5% SDS-PAGE, followed by staining with Coomassie Blue (lanes 1–3), or analysis by immunoblotting and autoradiography (lanes 4–12). Cross-reacting proteins of similar molecular weight are visible with D77 (lanes 5 and 6) and A66 (lane 12), but not with B15. Protein p38 is indicated by the arrow. The three nuclei preparations contain abundant histones (solid circles).

Using immunoblotting the existence of proteins similar to p38 in other organisms were investigated. Purified nuclei from rat liver were probed with monoclonals D77, D15, and A66 (FIG. 7). D77 recognizes a polypeptide of relative molecular weight 37,000 whereas B15 and A66 do not. The 37,000 molecular weight protein was the only protein identified by D77 even after long exposure of the autoradiogram. The low molecular weight protein recognized by A66 is probably histone H4.

Nuclei from *Neurospora crassa*, a fungus of the same taxonomic class as *S. cerevisiae*, were also analyzed. Nuclei of high purity were obtained using essentially the same method as for yeast. Interestingly, both D77 and A66 recognize an *N. crassa* protein that comigrates with p38 (FIG. 7). Similar to the case for rat liver, B15 does not cross react. In combination with the results from rat liver nuclei, the data from *N. crassa* suggest that D77, B15 and A66 bind to three different antigenic determinants. D77 appears to recognize an evolutionarily conserved epitope. Results similar to those obtained with N. crassa were achieved in an analysis of *Schizosaccharomyces pombe*. In the case of purified nuclei from a wild type strain of *S. pombe*, D77 and A66 recognized predominantly one protein of apparent molecular weight 35,000 by immunoblot.

Immunofluorescence Localization in Buffalo Rat Liver Cells

Figure 8A:
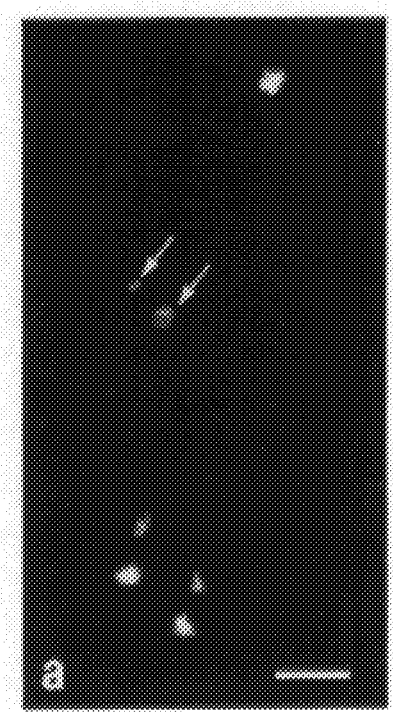
FIGS. 8(a) through 8(d) shows immunofluorescence localization of the D77 cross-reactive protein to the nucleolus of buffalo rat liver cells. Cultured BRL cells were examined using the monoclonal D77, or a control culture medium (C), and a fluorescein conjugated anti-mouse antibody. Comparison of the immunofluorescence (a and c) and phase contrast micrographs (b and d) reveals that D77 specifically recognizes a protein localized to the nucleolus (arrows). The staining pattern is noticeably fibrillar (a). Bar, 2 μm.
Figure 8B:
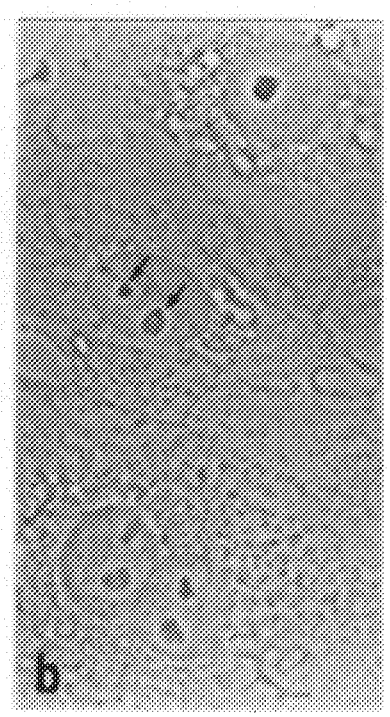
Figure 8C:
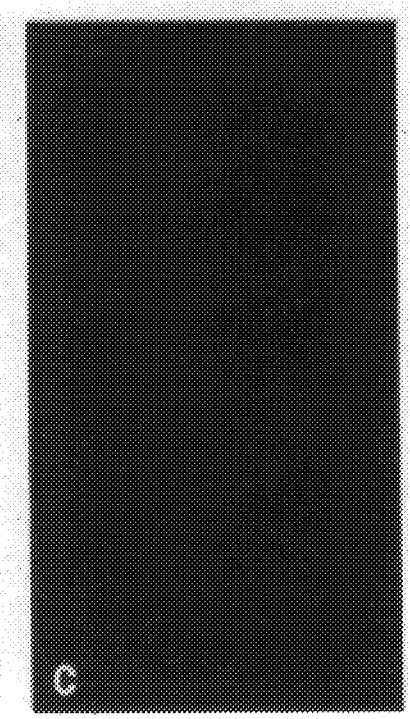
Figure 8D:
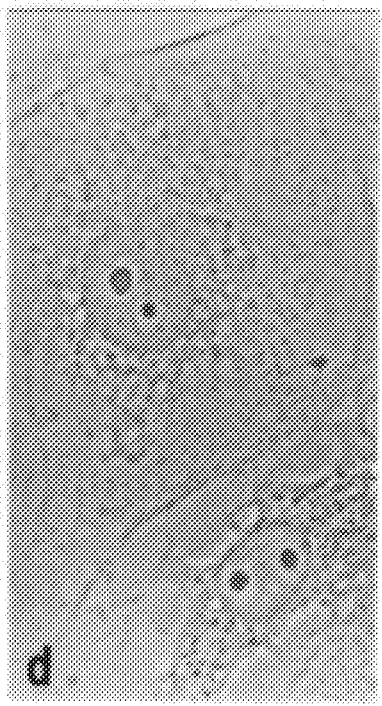

Immunoblotting with D77 suggested that the crossreacting protein in rat liver could be localized using indirect immunofluorescence. For this purpose rat liver (BRL) cells were grown in tissue culture, and prepared for immunofluorescence using standard procedures. It was observed that D77 produces a bright fluorescent signal coincident with the nucleolus (FIG. 8a). The nucleolus is identified by virtue of its darker appearance when observed with phase contrast (FIG. 8b). Examination of the fluorescence staining pattern in BRL cells shows that the entire nucleolus is not stained uniformly. Rather, the pattern appears convoluted or fibrillar (FIG. 8a). In comparison, B15 produces a very faint speckled intranuclear pattern, and A66 generated no fluorescence above background.

Figure 9:
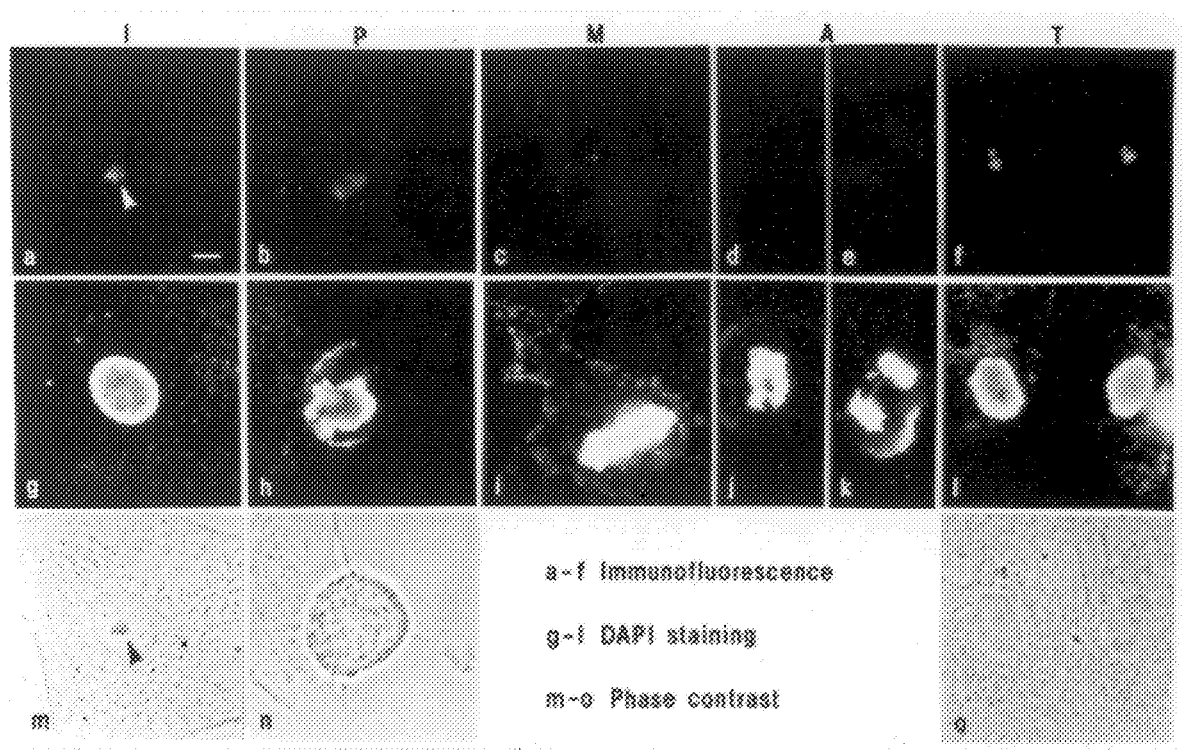
FIGS. 9(a)–9(o) present immunofluorescence localization of the D77 cross-reactive protein during mitosis in buffalo rat liver cells. Samples for immunofluorescence were prepared as in FIG. 8. Stages of the cell cycle (I, P, M, A, T) are shown visualized by fluorescence (a-f), DAPI staining of chromatin (g-l), or phase contrast (m-o). The nucleolus is indicated by the arrowhead. Small DAPI staining spots are mitochondria. Bar, 1.5 μm.
Figure 10A:
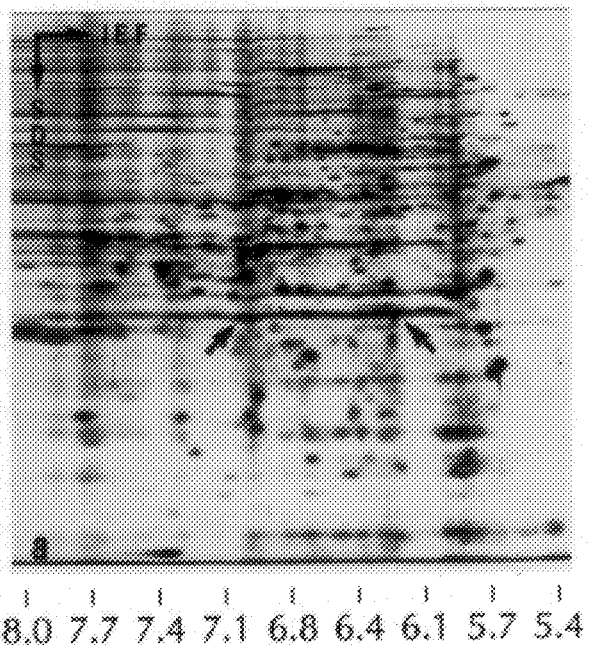
FIGS. 10(a) through 10(d) present a comparison of the yeast and rat liver nucleolar proteins using IEF (i.e., isoelectric focusing) two-dimensional gels. Two-dimensional IEF gels were run with purified yeast (a and c) and rat (b and d) liver nuclei samples, and silver stained (a and b) or immunoblotted with D77 (c and d). Portions of the stained proteins are detected with D77 (region between arrows). Numbers indicate pH values in IEF dimension.
Figure 10B:
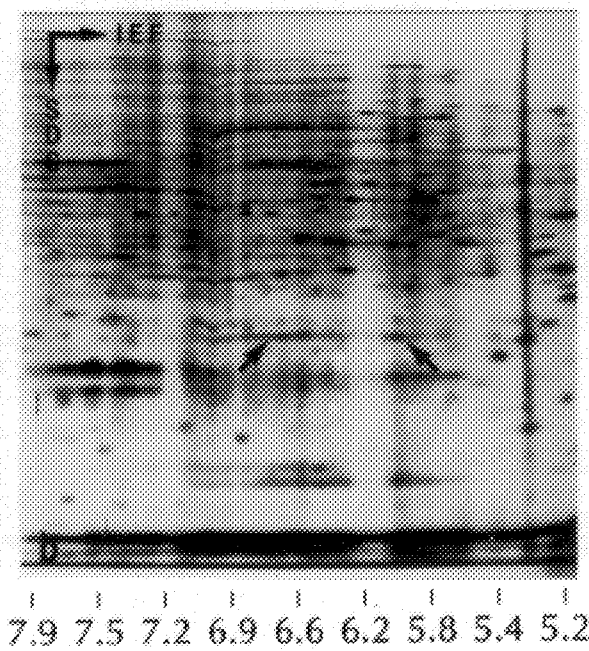
Figure 10C:
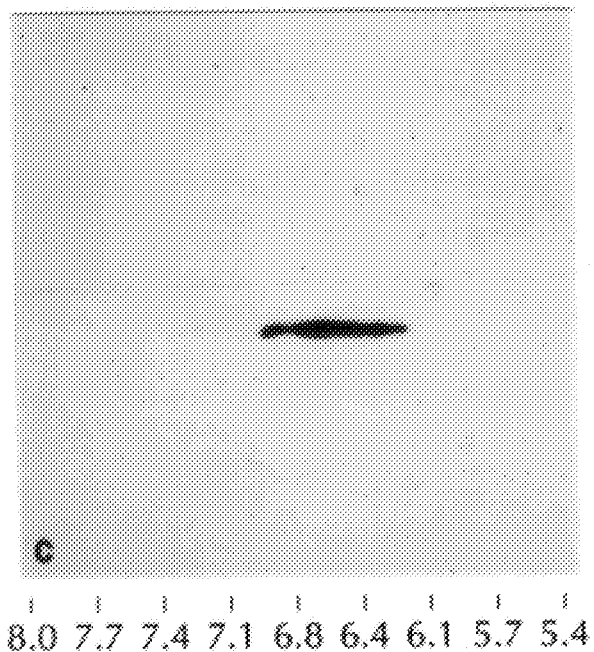
Figure 10D:
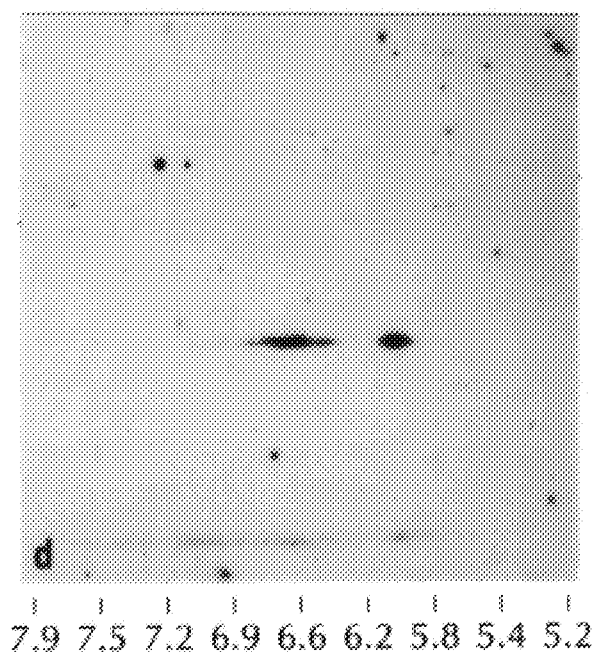
Figure 11A:
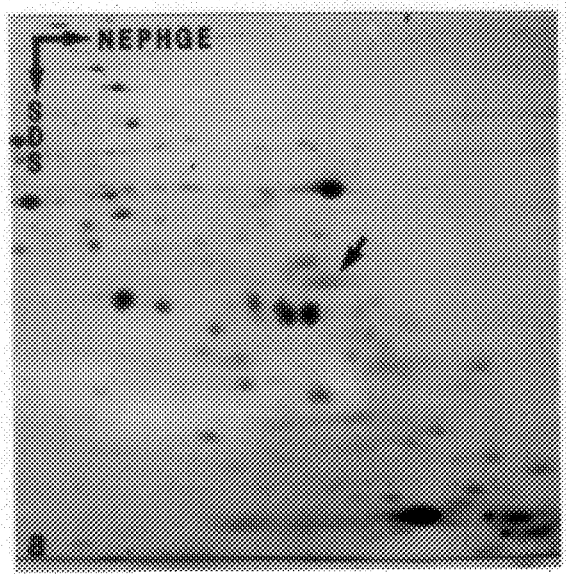
FIGS. 11(a) through 11(d) set forth a comparison of the yeast and rat liver nucleolar proteins using NEPHGE (i.e., nonequilibrium pH gradient electrophoresis) two-dimensional gels. Two-dimensional NEPHGE gels were run with purified yeast (a and c) and rat (b and d) liver nuclei samples, and stained with Coomassie Blue (a and b), or immunoblotted with D77 (c and d). Both the yeast and rat liver proteins focus into single, discrete spots (arrows). Yeast histones are denoted by solid circles.
Figure 11B:
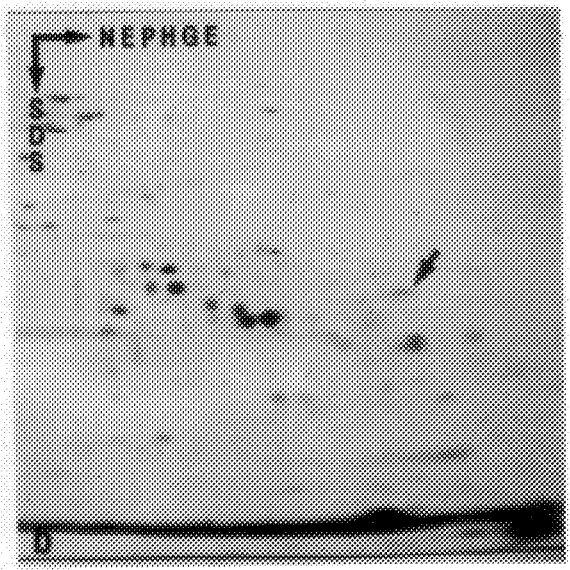
Figure 11C:
Figure 11D:
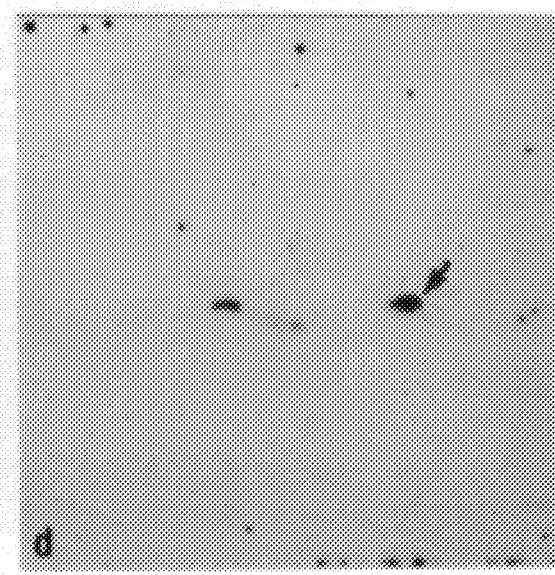

The D77 fluorescence became dispersed during mitosis in BRL cells (FIG. 9). Chromosomes in each of the mitotic stages were identified with DAPI staining. In prophase the D77 staining pattern became patchy, and by metaphase was uniformly cytoplasmic (FIG. 9, b and c). In late anaphase and early telophase, speckles of more intense fluorescence formed at the site of the chromosomes and probably represented early stages in nucleolar organization (FIG. 9, d–f).

Immunofluorescence performed on *N. crassa* with the D77 and A66 antibodies showed exclusively intranuclear staining, and B15 did not. The pattern was difficult to discern because the cell wall-less mutant of *N. crassa* that was used contained 10 to 20 relatively small nuclei per cell.

Characterization of p38 and the Rat Liver Nucleolar Protein by Two-dimensional Gel Electrophoresis The determination of isoelectric point is an important consideration in the comparison of p38 with the rat liver nucleolar protein, as well as with nucleolar proteins characterized in other studies. Purified nuclei from yeast and rat liver were digested with micrococcal nuclease at high pH, and subjected to IEF followed by SDS-PAGE (FIG. 10). Immunoblotting with D77 specifically identified the yeast and rat liver proteins of the correct molecular weight in each case, but showed the failure of either of the proteins to focus at a discrete isoelectric point. The D77 antigens were distributed between pI values of 6.2 and 6.9 in yeast, and 6.0 and 6.7 in rat liver (FIG. 10, c and d). Silver staining shows more pronounced streaking of the proteins than indicated by immunoblotting (FIG. 10 a and b). In addition, about 10% of the D77 antigens remained at the origin of the first dimension gels.

The majority of yeast and rat liver nuclear proteins detected by silver staining focus at discrete pI values (FIG. 10, a and b). Thus, the anomalous behavior of p38 and the rat liver nucleolar protein is not due to poor isoelectric focusing. Digestion of nuclei samples with DNase I and/or RNase A, omission of Triton X-100 detergent, use of zwitterionic (CHAPS) detergent, or a different pH range, do not improve the focusing of the IEF dimension.

To further characterize p38 and the rat liver protein we used NEPHGE followed by SDS-PAGE (FIG. 11). Samples of nuclear proteins were digested with micrococcal nuclease as for IEF gel electrophoresis. Both p38 and the rat liver nucleolar protein migrated as discrete spots in this twodimensional gel system. Immunoblotting with D77 detected p38 and the rat liver nucleolar protein as slightly elongate spots in each case (FIG. 11, c and d). The proteins identified by Coomassie blue staining exactly coincided with the D77 antigen. Interestingly, p38 and the rat liver protein migrated at a position expected for a basic protein. Proteins with basic pI values, such as histones, assume a position near the rightward edge of the protein pattern (FIG. 11a). No D77 antigen was observed at the origin, in contrast to the results with IEF electrophoresis.

This analysis of yeast p38 and the rat liver nucleolar protein demonstrates similar behavior of these proteins by two different two-dimensional gel methods. The measurement of pI has not been practicable, despite the use of various IEF conditions, and may be complicated by incomplete disruption of protein-ribonucleic acid interactions in the sample prepared for the first gel (see below). NEPHGE gives more uniform migration of p38 and the rat liver nucleolar protein than IEF. NEPHGE conditions are optimized for the resolution of basic proteins. The position of the nucleolar proteins in NEPHGE, and the improved focusing, suggest that p38 and the rat liver protein have basic pI values.

Immunologic Cross-reactivity between p38 and Vertebrate Nucleolar Proteins

In light of the cross-reactivity between p38 and the 37,000-mol-wt mammalian nucleolar protein, it was believed likely that antibody reagents directed against vertebrate nucleolar proteins might recognize p38. In addition, such reagents may establish the identity of the rat liver protein. A considerable amount of information was available on the immunoreactivity of several nucleolar proteins similar in size to p38. Thus, immunoblots were probed with three antibodies specific for the nucleolar proteins fibrillarin, NO38, and B23. Fibrillarin has been identified with a human serum from a patient with scleroderma autoimmune disease by Ochs et al. (Ochs, E. L., et al. (1985) Biol. Cell. 54:123–134). Monoclonal No-185 was generated by Schmidt-Zachmann et al., against the *Xenopus laevis* protein NO38 (1980, EMBO 6:1881–1890). Monoclonal B23 was generated against rat Novikoff hepatoma nucleoli by Busch and co-workers, and has been extensively characterized (Spector, D. L., et al. (1984) Chromosoma (Berl.) 90:139–148).

Figure 12:
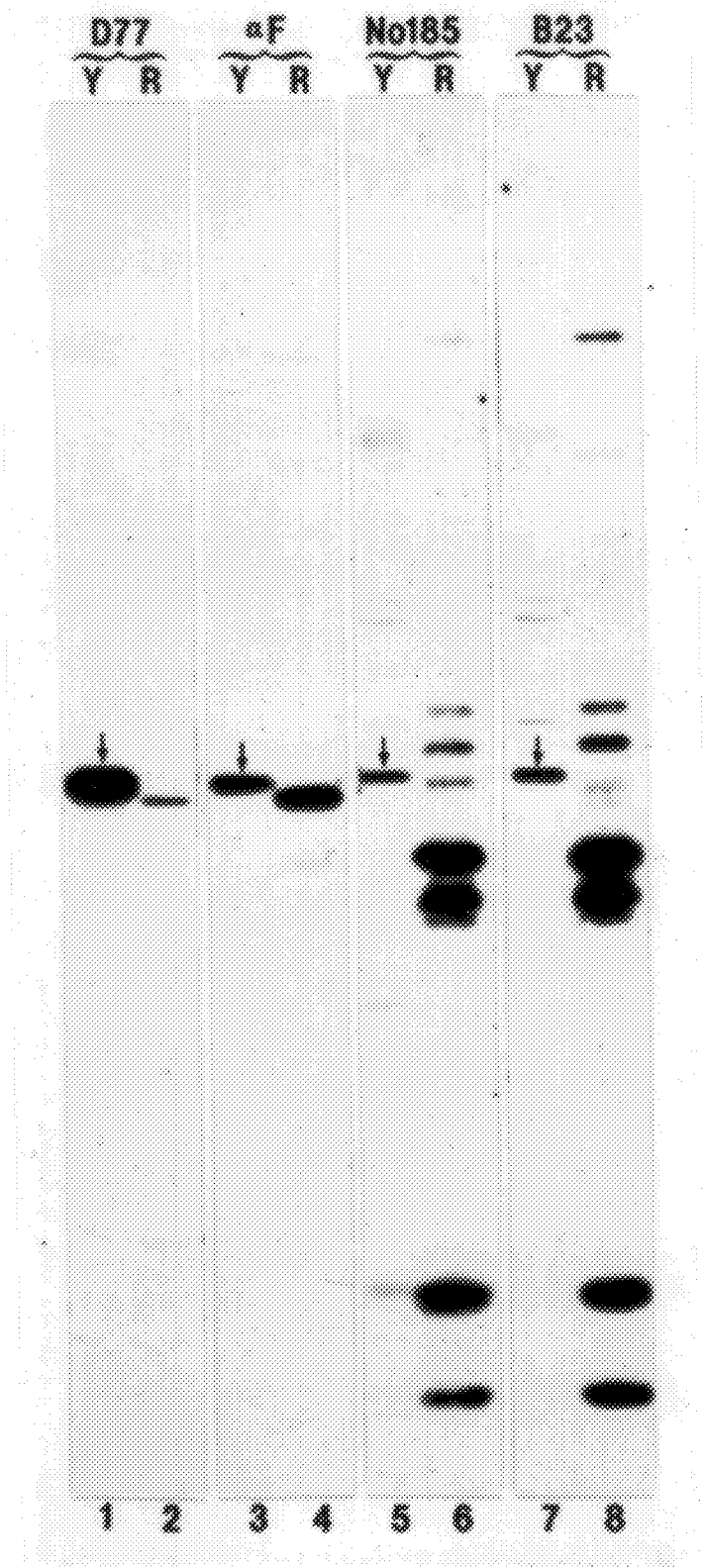
FIG. 12. Immunologic cross-reactivity between p38 and vertebrate nucleolar proteins. Yeast nuclei (Y, 50 μg protein) and rat nuclei (R, 10 μg protein) were electrophoresed on a 10.5% gel and analyzed by immunoblotting and autoradiography. Monoclonal D77, and the anti-fibrillarin autoimmune antiserum (αF) showed specific decoration of p38 (arrows) and the 37,000-mol-wt rat liver protein. Monoclonal No-185, which is specific for the NO38 nucleolar protein of *Xenopus laevis*, and the monoclonal B23, which is specific for the rat B23 nucleolar protein, show less reactivity with p38 (arrows), and a different pattern of reactivity towards proteins of rat liver nuclei.

Interestingly, all of the antibodies tested against yeast nuclear proteins show relatively specific reactivity with p38 (FIG. 12). The anti-fibrillarin antibody appears to show the strongest cross-reactivity with p38. The results with the rat liver nuclear proteins are markedly different. The anti-fibrillarin antibody detects the same 37,000-mol-wt protein in rat liver as detected by D77, by one-dimensional SDS-PAGE. However, monoclonals No-185 and B23 do not recognize the 37,000-mol-wt protein, and bind to a number of rat liver proteins, most prominent of which are some of the histones. The specificities of No-185 and B23 toward rat liver proteins are noticeably similar.

Taken together, these data suggest that p38 contains at least two epitopes that are shared with nucleolar proteins from higher cells especially mammalian cells; (i) the anti-fibrillarin epitope, and (ii) the No-185 and B23 epitope. Furthermore, the 37,000-mol-wt rat liver polypeptide is probably fibrillarin. Fibrallarin is known to have a basic pI and is distributed throughout the cell during mitosis (Ochs, R. L., et al. (1985) Supra). The rat liver protein detected by D77 exhibits the same behavior during mitosis and appears to have a basic pI (FIGS. 10–12).

The protein p38 is an authentic nucleolar component and does not appear to be present in the mature ribosome, as indicated by immunoblot analysis of subcellular fractions and indirect immunofluorescence. However, the possibility that p38 is a component of a nuclear preribosomal particle cannot be ruled out. Consistent with its assignment to the nucleolus, p38 is not an integral membrane protein. The susceptibility of intranuclear proteins to extraction with high concentrations of salt or urea, but not with nonionic detergent, is a general phenomenon observed with nuclei purified from vertebrate cells as well as yeast (Davis, L. I., et al. (1986) Cell 45:699–709 and Wu, L-C., et al. (1987) J. Biol. Chem. 262:883–891). Immunofluorescence experiments with mitotic yeast cells support the notion that p38 is a nucleolar constituent. During mitosis, p38 appears to remain associated with the chromatin and attached to the nuclear envelope in the form of a distinctly crescent-shaped region. Early in mitosis the nuclear envelope begins to elongate into the growing bud as the spindle pole bodies separate, and the extension of the envelope towards the bud is relatively free of chromatin (Gordon, C. N. (1977) J. Cell. Sci. 24:81–93). Likewise, p38 and the nucleolus in general, remain at a location separate from this extension, and only enter the daughter cell after the chromatin begins to distribute in the same way. Mitosis in yeast is known to involve such a delay in the partitioning of the chromosomes into the daughter cell until an advanced stage of mitosis, and studies of chromatin distribution during yeast mitosis have shown similar behavior for the nucleolus (Gordon, C. N. (1977) Supra). The continued association between the nucleolus and nuclear envelope during mitosis has been demonstrated at the electron microscope level (Gordon, C. N. (1977) Supra). Towards the conclusion of nuclear division, the neck region of the dividing nucleus becomes depleted in chromosoma content (Gordon, C. N. (1977) Supra). Protein p38 is found in the neck region as the chromosomes separate during the middle stages of mitosis, but is absent from the neck after the chromosomal masses have begun their reorganization late in mitosis. The same behavior of the nucleolus has been observed by electron microscopy during mitosis (Gordon, C. N. (1977) Supra). Finally, immunogold electron microscopy unequivocally locates p38 to the nucleolus. It is not clear if p38 is organized into, or associated with, a fibrillar structure of the yeast nucleolus.

An interesting aspect of the variation in specificity of the monoclonals raised to p38 emerges from the subcellular fractionation experiments and the indirect immunofluorescence data. Monoclonal A66 detects a small amount of p38 in nonnuclear locations, such as the endoplasmic reticulum, and exhibits greater specificity than D77 or B15 for p38 in nonnuclear locations. In addition, A66 preferentially decorates the periphery, or "rim", of the nucleolus. One explanation is that more than one gene encodes a group of very similar p38 proteins, that assume slightly different intracellular distributions. Alternatively, p38 may participate in the delivery of ribosomal proteins to the nucleolus, or the delivery of mature ribosomes to the endoplasmic reticulum, and a subset of p38 moleculares may cycle between the endoplasmic reticulum and the nucleolus. It is also conceivable that A66, and perhaps B15, recognizes an epitope present on a precursor form of p38, which is altered among p38 molecules after incorporation into the nucleolus.

One of the monoclonals against p38, D77, cross reacts with a rat liver nucleolar protein of molecular weight 37,000. In addition, p38 shares two different epitopes with a 38,000-mol-wt nuclear protein from *Neurospora crassa*. The similarity between p38 and rat liver nucleolar protein is extensive. Two-dimensional IEF/SDS-PAGE shows that both the yeast and rat liver nucleolar proteins adopt a distribution to a similar range of isoelectric points in the IEF dimension. The positions of each protein in NEPHG/SDS-PAGE two-dimension gels are nearly identical and indicative of proteins with basic pI values. The failure of p38 or the rat liver protein to focus into a discrete spot by IEF/SDS-PAGE may be explained by association with nucleic acid and/or extensive modification (possibly phosphorylation). A tight association between a nucleolar protein and RNA may not be interrupted by isoelectric focusing. Consistent with this possibility is the participation of fibrillarin in the U3 RNP particle (Reimer, G., (1987) Arth. Rheum. 30:793–800).

The 37,000-mol-wt protein from the rat liver nucleolus is most likely the fibrillarin counterpart in rat liver. The D77 antigen in rat liver is distributed throughout the cytosol during mitosis, and appears to have a basic pI. Fibrillarin exhibits the same behavior during mitosis, and the purified protein has a pI of 8.5 (Ochs, R. L., et al. (1987) Supra). This is the pI of human p38 as well (yeast p38 has a pI of about 10). Moreover, both D77 and anti-fibrillarin antibodies recognize the same 37,000-mol wt protein from rat liver. By comparison, the nucleolar proteins NO38 and B23 remain associated with chromosomes, presumably the NOR, during mitosis (Schmidt-Zachmann, M. S. (1987) Supra and Spector, D. L. (1984) Supra). The nucleolar proteins NO38 and B23 have pI values of 5.6 and 5.5 respectively. Although fibrillarin in rat liver has not been previously characterized, fibrillarin occurs in nucleoli from many cells sources, including human HeLa cells and lymphocytes, mouse 3T3 cells, frog (Xenopus) A6 cells, and rat kangaroo PtK2 cells (Ochs, R. L., et al. (1985) Supra).

Like the nucleolus of higher cells, the yeast nucleolus consists of a fibrillar network associated with other densely staining material when observed in the electron microscope (Molenaar, T., et al. (1970) Exp. Cell Res. 60:148–156). In higher cells, however, more ultrastructural definition is apparent in the form of the granular component and fibrillar centers (Fakan, S., et al. (1986) Supra; Goessens, C. (1984) Supra and Hadjiolov, A. A. (1985) Supra). Fibrillarin, as its name implies, is located in the fibrillar component of higher cell nucleoli (Ochs, R. L., et al. (1985) Supra). NO38 and B23 are proteins of the granular component (Schmidt-Zachmann, M. S. (1987) Supra and Spector, D. L. (1984) Supra). Yeast p38 and fibrillarin share at least one epitope, in addition to similar physical properties. Although p38 appears to be most similar to fibrillarin, it shares at least one other epitope with other vertebrate nucleolar proteins. It is tempting to speculate that p38 may combine functional specializations that are segregated into different proteins and/or ultrastructural subcompartments of the nucleolus in higher cells.

The monoclonal antibodies D77, B15 and A66 specifically recognize a protein component of the nucleolus of human and other cell types. D77 reacts with human cells, particularly the nucleolar protein as tested by Western blot and immunofluorescence assays.

These monoclonals are mouse antibodies. However, using similar techniques human or other mammalian antibodies can be developed. Thus the invention cannot be limited to the examples shown. Other embodiments will suggest themselves to those skilled in the art. These monoclonals are on deposit at Rockefeller University, Laboratory of Cell Biology, Howard Hughes Medical Institute, The Rockefeller University, New York, N.Y. 10021.

Hybridoma cell line D77 has been deposited at the American Type Culture Collection, 12301 Parklawn Drive, Rockville Md., 20852, since Jul. 19, 1995, and has been accorded Accession Number HB 11956.

These monoclonal antibodies can be used for example as positive control antibodies in a test kit used with an indirect immunofluorescence test in a clinical diagnosis of the autoimmune disease scleroderma (systemic sclerosis), systemic lupus erythematosus and other autoimmune diseases. These test kits can also be used for Western blot analysis.

The monoclonals can be modified for example by fluorescein to be fluorescent labelled monoclonals.

These monoclonals would then be part of a test kit for auto-immune disease to serve as the control in determination of auto-immune disease wherein the kit is directed to anti-nucleolar antigen as is used in clinical applications for the diagnosis and management of systemic lupus Erythematosus and other rheumatic diseases and scleroderma.

One or more of the monoclonal antibodies of the invention would serve as a base line since it is now known to react with nucleolar protein. Thus no human antibody need be used. This serves to eliminate any risk (AIDS, hepatitis) where a human blood product is used or handled. The human blood product is also subject to batch-to-batch variation whereas the monoclonal is not. Thus test results will be compared against a common, constant base line.

Thus these anti-nucleolar test kits achieve safety and constancy factors not met in previous test kits.

What is claimed:

1. Monoclonal antibody which specifically binds to yeast fibrillarin.

2. The monoclonal antibody of claim 1, wherein said monoclonal antibody also binds to human fibrillarin and is designated HB 11956.

3. Hybridoma cell line which produced a monoclonal antibody which specifically binds to yeast fibrillarin.

4. The hybridoma cell line of claim 3, wherein said monoclonal antibody binds to both yeast fibrillarin and human fibrillarin and is designated HB 11956.

5. Test kit useful in diagnosing scleroderma, comprising:
   (i) a positive control reagent which comprises monoclonal antibody designated HB11956 which specifically binds to both human fibrillarin and to yeast fibrillarin; and
   (ii) a receptor which specifically binds to said monoclonal antibody which specifically binds to said human fibrillarin.

6. The test kit of claim 5, further comprising a solid phase which has immobilized thereon a sample of said human fibrillarin.

7. The test kit of claim 5, wherein said receptor is a second antibody which specifically binds to said monoclonal antibody.

8. The test kit of claim 7, wherein said second antibody is labelled fluorescently, enzymatically or chromophorically.

* * * * *